United States Patent [19]

Jorgenson et al.

[11] Patent Number: 5,713,885
[45] Date of Patent: Feb. 3, 1998

[54] ABSORBENT ARTICLE HAVING AN INTEGRAL BARRIER

[75] Inventors: Thomas Patrick Jorgenson, Neenah; Lori Sue Schutkoske, Buttes des Morts, both of Wis.

[73] Assignee: Kimberly-Clark Worldwide, Inc., Neenah, Wis.

[21] Appl. No.: 656,734

[22] Filed: Jun. 3, 1996

Related U.S. Application Data

[63] Continuation-in-part of Ser. No. 366,868, Dec. 30, 1994, abandoned.

[51] Int. Cl.$^6$ .................................................. A61F 13/15
[52] U.S. Cl. ..................... 604/385.2; 604/387; 604/385.1
[58] Field of Search ......................... 604/369, 377, 604/378, 380, 384, 385.1, 385.2, 387, 43, 53; 128/849, 853, 888, 889

[56] References Cited

U.S. PATENT DOCUMENTS

| | | | |
|---|---|---|---|
| Re. 33,351 | 9/1990 | Papajohn | 604/387 |
| 75,038 | 3/1868 | Manheim . | |
| 709,223 | 9/1902 | James et al. . | |
| 810,128 | 1/1906 | Green . | |
| 810,130 | 1/1906 | Green . | |
| 810,133 | 1/1906 | Green . | |
| 2,069,092 | 1/1937 | Jackson, Jr. . | |
| 2,331,271 | 10/1943 | Gilchrist . | |
| 2,507,197 | 8/1950 | Matzdorf | 604/377 |
| 3,211,147 | 10/1965 | Pherson et al. . | |
| 3,295,526 | 1/1967 | Sabee . | |
| 3,364,931 | 1/1968 | Hirsch . | |
| 3,525,337 | 8/1970 | Simons . | |
| 3,572,342 | 3/1971 | Lindquist et al. . | |
| 3,575,174 | 4/1971 | Mogor . | |
| 3,699,966 | 10/1972 | Chapuis . | |
| 3,863,637 | 2/1975 | MacDonald et al. . | |
| 3,954,107 | 5/1976 | Chesky et al. . | |
| 4,389,211 | 6/1983 | Lenaghan . | |
| 4,451,934 | 6/1984 | Gioello . | |
| 4,505,704 | 3/1985 | Roeder . | |
| 4,559,050 | 12/1985 | Iskra . | |
| 4,578,068 | 3/1986 | Kramer et al. . | |
| 4,578,070 | 3/1986 | Holtman . | |
| 4,657,539 | 4/1987 | Hasse . | |
| 4,753,644 | 6/1988 | Cottenden et al. | 604/378 |
| 4,781,711 | 11/1988 | Houghton et al. | 604/378 |
| 4,840,692 | 6/1989 | Kamstrup-Larson | 156/252 |
| 4,892,535 | 1/1990 | Bjornberg et al. | 604/380 |
| 4,935,021 | 6/1990 | Huffman et al. | 604/385.1 |
| 4,940,462 | 7/1990 | Salerno | 604/387 |
| 5,066,527 | 11/1991 | Newell | 428/35.6 |
| 5,151,091 | 9/1992 | Glaug et al. | 604/385.1 |
| 5,207,662 | 5/1993 | James | 604/385.2 |
| 5,207,664 | 5/1993 | Blanco | 604/385.2 |
| 5,211,641 | 5/1993 | Roos et al. | 604/385.1 |
| 5,267,992 | 12/1993 | Van Tilburg | 604/387 |
| 5,423,786 | 6/1995 | Fung et al. | 604/367 |
| 5,429,633 | 7/1995 | Davis et al. | 604/387 |

FOREIGN PATENT DOCUMENTS

| | | | |
|---|---|---|---|
| 152972 | 3/1938 | Austria | 604/378 |
| 0 130 848 A2 | 1/1985 | European Pat. Off. . | |
| 0 520 884 A1 | 12/1992 | European Pat. Off. . | |
| 0529641A1 | 3/1993 | European Pat. Off. . | |
| 0532035A3 | 3/1993 | European Pat. Off. . | |
| 2023067 | 12/1979 | United Kingdom . | |
| 2100130 | 12/1982 | United Kingdom . | |
| 2 209 672 | 5/1989 | United Kingdom . | |
| 2263914 | 8/1993 | United Kingdom . | |
| WO92/07536 | 5/1992 | WIPO . | |

*Primary Examiner*—John M. Weiss
*Assistant Examiner*—Karin M. Reichle
*Attorney, Agent, or Firm*—Mark L. Davis

[57] ABSTRACT

An absorbent article is provided having a liquid-permeable cover, a liquid—impermeable baffle and an absorbent with longitudinal side portions positioned intermediate thereof. The cover and/or baffle can extend beyond the longitudinal side portions to form longitudinal side edges of the absorbent article. The absorbent article further includes integral side barriers formed by gathering the longitudinal side edges inward toward the absorbent. In a preferred embodiment, the integral, longitudinal side barriers have a tensioning member for imparting a curved configuration to the absorbent article.

19 Claims, 4 Drawing Sheets

ABSORBENT ARTICLE HAVING AN INTEGRAL BARRIER

This application is a continuation-in-part of application Ser. No. 08/366,868, entitled "ABSORBENT ARTICLE HAVING AN INTEGRAL BARRIER" and filed in U.S. Patent and Trademark Office on Dec. 30, 1994 now abandoned. The entirety of that application is hereby incorporated by reference.

FIELD OF THE INVENTION

This invention relates generally to disposable absorbent articles for absorbing body fluid and in particular to sanitary napkins for absorbing menstrual fluid. More particularly, the present invention relates to sanitary napkins having an integral fluid barrier positioned along the longitudinal sides thereof.

BACKGROUND OF THE INVENTION

All manner and variety of absorbent devices or appliances have been configured for the absorption of body fluids, such as menses, and are well known. Such devices are expected to absorb the body fluid, retain the fluid within the absorbent and to prevent the discharged body fluids from soiling the person's body and/or adjacent clothing.

In the formation of such disposable absorbent devices they commonly include a liquid-permeable bodyfacing cover, an absorbent core and a liquid-impermeable backing sheet or baffle. These absorbent devices, whether utilized as diapers, incontinence garments or sanitary napkins are subject to failure. Leakage from absorbent devices is generally attributed to a high concentration of fluid absorption at the point of fluid insult. This could be the result of a sudden release of body fluid onto the absorbent device, overloading its absorption capability; or the result of a prolonged, steady discharge which may have caused the absorbent material in the device to become super-saturated and unable to accept, to a large degree, additional fluids from the body. Using a sanitary napkin as an example, menses will generally migrate radially from the point of insult and will leak from the sides. This usually results in soiling the wearer's body, typically around the thigh region, and the undergarment.

In the area of sanitary napkins, it has been suggested that at least 20–25 percent of all sanitary napkins experience side leakage. One reason for this is that, when worn, the sanitary napkin can become deformed due to dynamic forces generated as the wearer moves or alters her stationary position. The greatest deformation normally occurs within that part of the article which, in use, is located in the narrowest space between the wearers thighs. Generally, the sanitary napkin deforms by bunching, twisting, and roping which are all well known in the art. As a result of the deformation the surface area of the sanitary napkin is greatly reduced.

To overcome the problem of side leakage, sanitary napkins have been constructed having elasticized sides that urge the sides upward or cause the sanitary napkin to form a cup shape.

Another method of preventing side leakage has been to extend wings, flaps or panels (hereinafter wings) from the edges of the sanitary napkin. The wings generally extend over the edges of the undergarment and are intended to adhere to the underside of the crotch portion or to themselves. The wings typically assist the garment adhesive, if present, to hold the sanitary napkin in position during use. To some extent, the wings counteract deformation of the sanitary napkin since they are anchored to the longitudinal edges of the undergarment. The wings also form a guard against side leakage and minimize soiling the wearer's undergarment.

In some cases, such as when the sanitary napkin is positioned crookedly, or when it becomes wrinkled or folded, wings can fold inward, partially occluding the fluid receiving surface. This diminishes the efficacy of the sanitary napkin to absorb discharged body fluids. At other times, the wings can contribute to an incidence of failure. This can occur because the wings generally are intended to form liquid barriers and seldom contain any absorbent material. Thus, the wings act as a transporting means to spread over a large area any body liquids reaching them.

Improving the performance of sanitary napkins continues to be a formidable undertaking, although a number of improvements have been made in both materials and construction. However, eliminating leakage, particularly along the inside of the thighs without compromising comfort and fit has not yet met the desired needs of the consumer.

Therefore, there remains a need for a sanitary napkin that will be comfortable to wear while decreasing the chance of side leakage associated with the use of sanitary napkins during the menstrual period.

SUMMARY OF THE INVENTION

Briefly, this invention relates to disposable absorbent articles, and more particularly, to sanitary napkins which are designed to absorb body fluids, such as menstrual fluid, and other excrements discharged by the body during a menstrual period. The present invention provides an absorbent article having improved side leakage protection.

Broadly, this invention provides for an absorbent structure having an integral barrier device. In one embodiment, an absorbent structure is provided having a longitudinal central axis, a liquid-permeable body-facing surface superposed over a liquid-impermeable garment-facing surface. The body-facing surface and the garment-facing surface extend laterally outward relative to the longitudinal axis to form longitudinal edges. The longitudinal edges are wound to form integral, longitudinal barriers.

In another embodiment, an absorbent article is provided having an absorbent adapted to reside adjacent to the wearer. The absorbent has a liquid-permeable body-facing surface and a garment-facing surface. Secured to the garment-facing surface is a liquid-impermeable baffle. Preferably, the baffle has a width greater than the absorbent and extends laterally outward to define longitudinal edges of the absorbent article. The longitudinal edges are gathered to form integral, longitudinal barriers. The absorbent article can include other features such as a cover and a resilient layer.

In another embodiment, a sanitary napkin is provided having a liquid-permeable cover with a body-facing surface, a liquid-impermeable baffle and an absorbent positioned between the cover and the baffle. The absorbent has longitudinal side portions. The cover and/or baffle extend laterally outward from the longitudinal side portions to define a pair of longitudinal edges of the sanitary napkin. The longitudinal edges are gathered and preferably, spirally wound to form integral longitudinal barriers. The integral barriers include tensioning means for imparting an arcuate shape to the absorbent structure. By "arcuate" it is meant that when the absorbent structure is placed on a flat or planar surface at least one of the transverse ends will be spaced above the surface.

It is a general object of this invention to provide an absorbent structure having improved side leakage protection and is comfortable to wear. A more specific object of this invention is to provide an improved absorbent article having integral fluid barriers.

Another object of this invention is to provide an absorbent article having integral longitudinal barriers formed by the gathering of the laterally extending, longitudinal sides of the absorbent article.

It is another object of this invention to provide a curved sanitary napkin having an integral barrier. The barrier is formed by rolling the longitudinal sides of the sanitary napkin. The integral barrier has secured to it a tensioning means for bending the integral barrier into a concave shape toward the body-facing surface of the sanitary napkin.

These and other objects, features and advantages are readily apparent when considered in reference to the following specification and the accompanying drawings. It is to be understood that the invention is not to be considered limited to the constructions disclosed except as determined by the scope of the appended claims.

DETAILED DESCRIPTION OF THE PREFERRED EMBODIMENT

Figure 1:
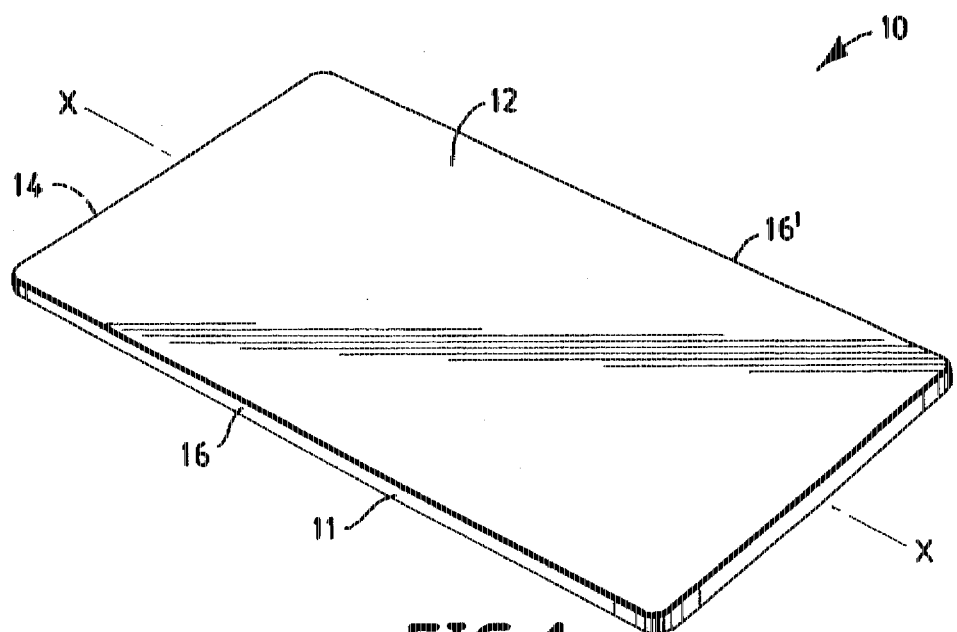
FIG. 1 is a top perspective view of an absorbent structure showing longitudinal side portions extending laterally outward relative to a longitudinal centerline X—X.
Figure 2:
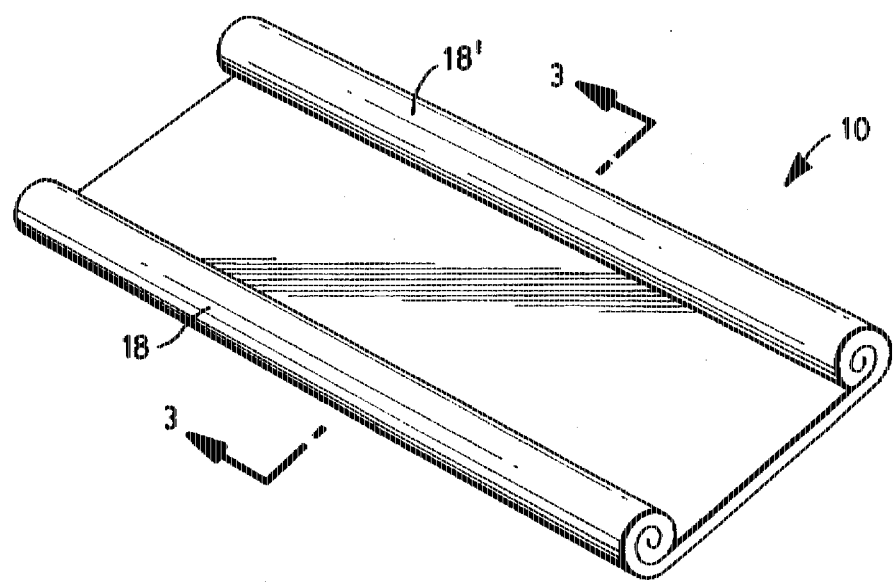
FIG. 2 is a top perspective view of the bodyfacing surface of the absorbent structure shown FIG. 1 illustrating the resulting configuration of the side barriers.

Although described hereafter as a sanitary napkin, it is understood that the invention can be adapted for use in disposable diapers, adult incontinence devices, training pants and the like. In the various views, similar components therein will be differentiated by the use of a prime (') symbol.

Referring to FIGS. 1–3A, an absorbent structure 10 is provided having a longitudinal central axis X—X, an absorbent 11, a liquid-permeable body-facing surface 12 and a liquid-impermeable garment-facing surface 14. The body-facing surface 12 is superposed over at least a portion of the garment-facing surface 14. Preferably, the body-facing surface 12 and the garment-facing 14 are coextensive.

Extending laterally outward from the longitudinal central axis X—X of the absorbent structure 10 are longitudinal side edges 16 and 16'. The longitudinal side edges 16 and 16' are gathered together to form integral longitudinal side barriers 18 and 18'. Preferably, the side barriers 18 and 18' are formed by rolling the longitudinal edges 16 and 16', and more preferably, spirally winding the longitudinal side edges 16 and 16' inward toward the longitudinal central axis X—X. The longitudinal edges 16 and 16' can be spirally wound toward the garment-facing surface 14 but preferably are wound toward the bodyfacing surface 12.

Spirally winding the longitudinal side edges 16 and 16' is advantageous because it produces an outer configuration that is rounded and less likely to chaff and irritate the sensitive tissues in the thigh and crotch region of the wearer during use. Spirally winding the longitudinal edges 16 and 16' also produces a barrier 18 or 18' that is uniform. Other methods suitable for forming a barrier include folding the longitudinal edges 16 and 16' a predetermined number of times along one or more longitudinal fold lines to produce an accordion configuration (not shown).

The absorbent structure 10 can be produced by using a known absorbent, discussed in greater detail below. The garment-facing surface 14 can be a portion of the absorbent rendered hydrophobic by coating or impregnating the absorbent with a suitable material. One such material is a liquid latex that, when added, forms a hydrophobic surface.

Figure 3:
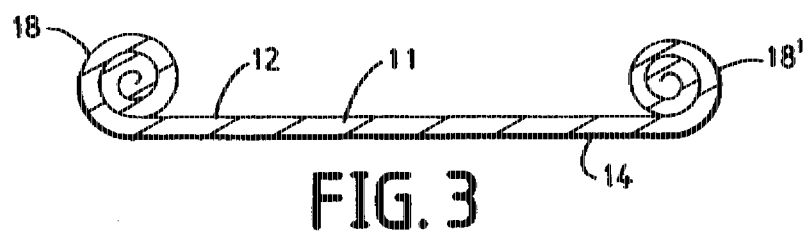
FIG. 3 is a cross-sectional view of the absorbent structure shown in FIG. 2 taken along line 3—3 of FIG. 2.
Figure 3A:
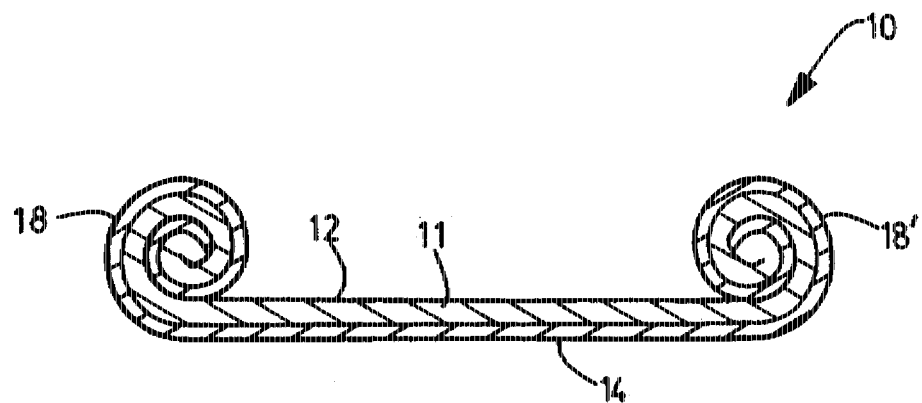
FIG. 3A is a cross-sectional view of an alternative embodiment of the absorbent structure incorporating a liquid-impermeable member.

Referring to FIG. 3A, the garment-facing surface 14 can include a separate, liquid-impermeable member such as a polyethylene film baffle discussed in greater detail below. The absorbent 11 and the baffle 14 are coextensive. Barriers 18 and 18' are formed by spirally winding the coextensive longitudinal edges 16 and 16' of the absorbent 11 and baffle 14.

Referring to FIGS. 4–10, disposable absorbent articles 100 and 200 of the present invention are illustrated in the form of a sanitary napkin 100 and 200 and are meant to be exemplary only and should not be deemed as limiting the scope of the present invention. Typically, a sanitary napkin is worn by a female to absorb body fluids, such as menses, blood, urine and other body excrements discharged during a menstrual period.

Figure 4:
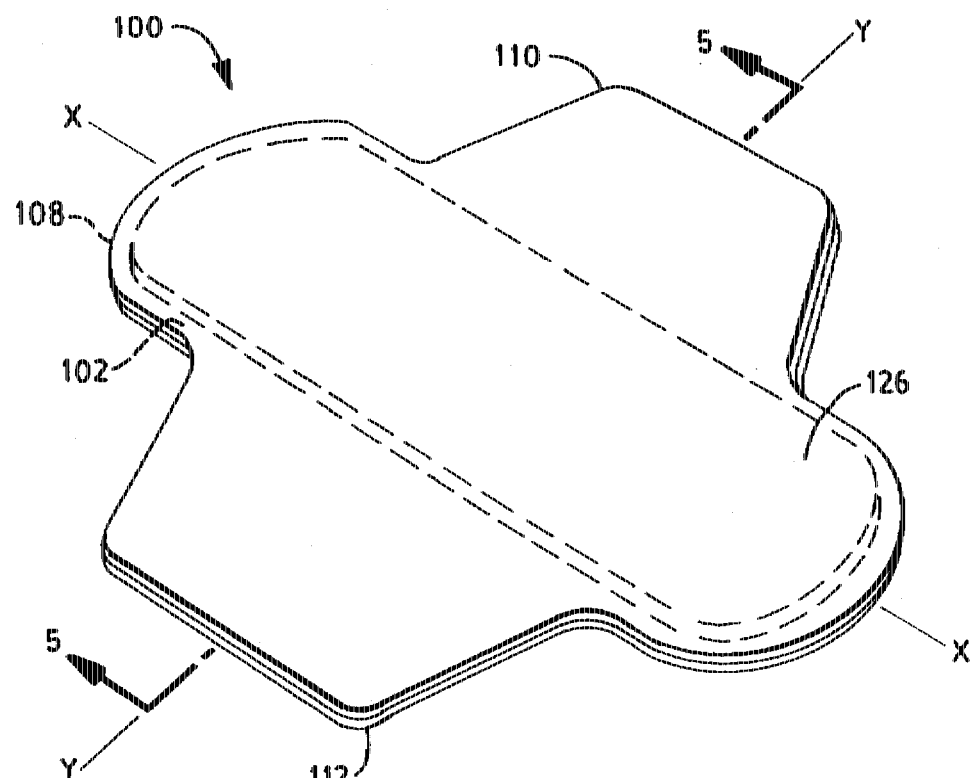
FIG. 4 is a top perspective view of an absorbent article illustrating non-linear longitudinal side portions extending laterally.
Figure 5:
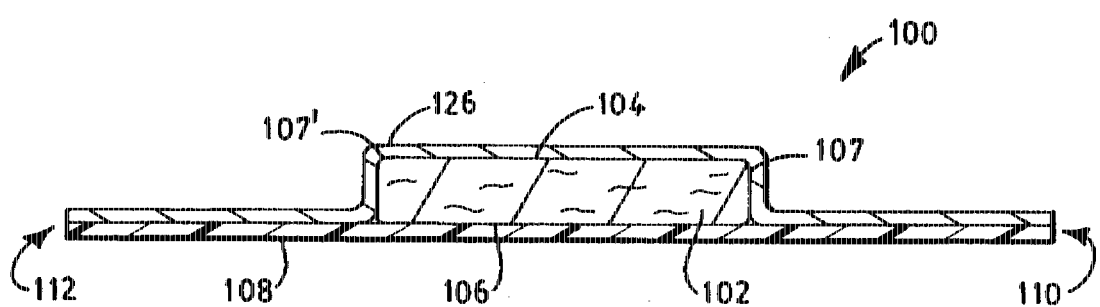
FIG. 5 is a cross-sectional view of the absorbent article shown in FIG. 4 illustrating the longitudinally extending sides prior to being gathered to form the side barriers.
Figure 6:
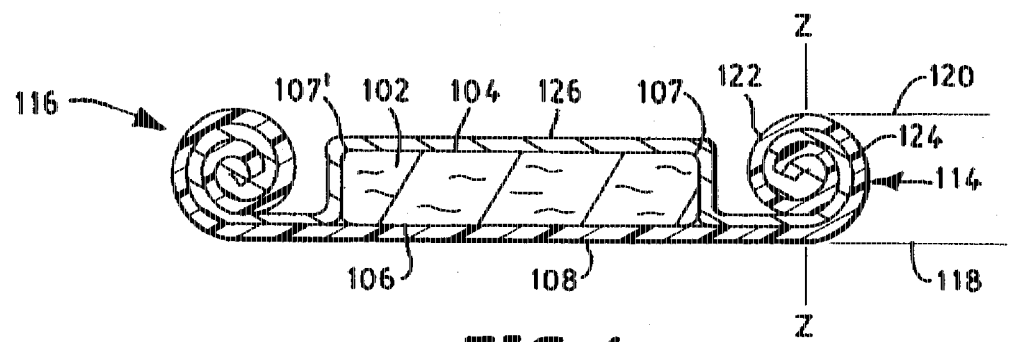
FIG. 6 is a cross-sectional view of the absorbent article shown in FIG. 4 illustrating the resulting configuration of the side barrier.
Figure 7:
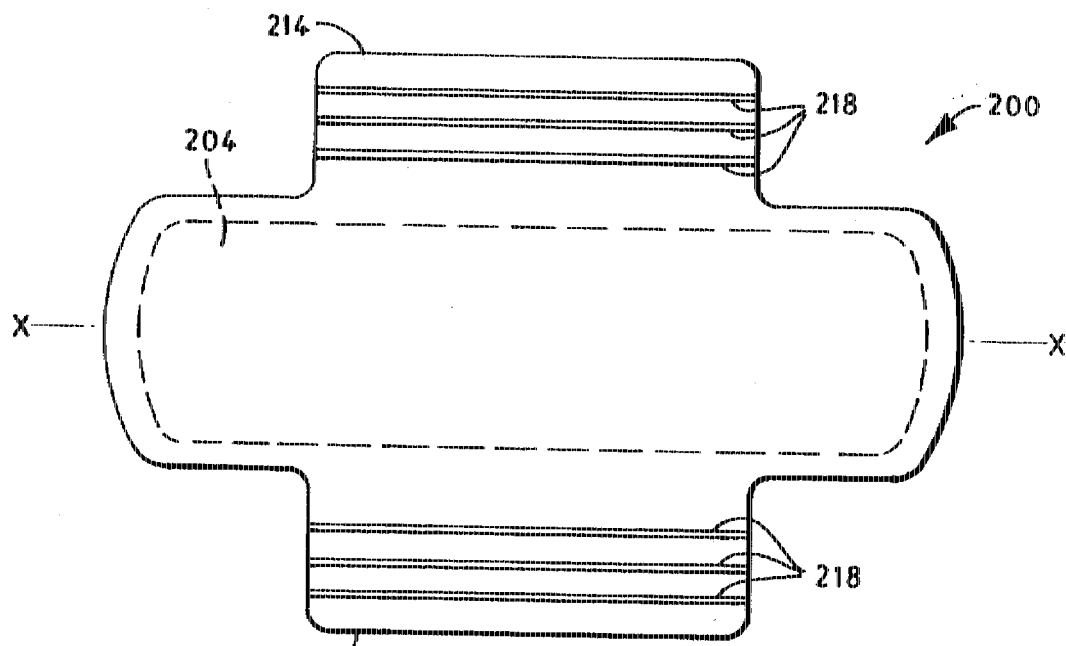
FIG. 7 is a top plan view of the bodyfacing surface of another absorbent article prior to forming the integral side barrier, illustrating non-linear longitudinal side portions extending laterally outward from an absorbent and tensioning means for bending the absorbent article.
Figure 8:
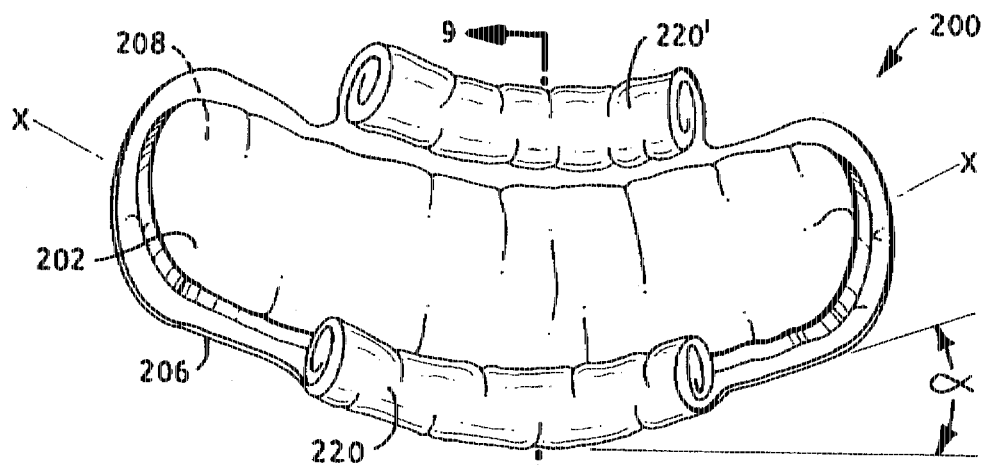
FIG. 8 is a top perspective view of the absorbent structure shown in FIG. 7 illustrating the resulting concave configuration of the absorbent structure.

Referring to FIGS. 4–6, a sanitary napkin 100 is provided having an absorbent 102. The absorbent 102 has a body-facing surface 104, a garment-facing surface 106 and longitudinal side portions 107 and 107'.

The body-facing surface 104 is disposed toward the wearer's body and adapted to reside adjacent to the wearer in use. The garment-facing surface 106 is disposed distal from the body-facing surface 104 and is adapted to reside adjacent to the wearer's undergarment. Secured to a garment-facing surface 106 is a liquid-impermeable baffle 108. Desirably, the baffle 108 has a width greater than the absorbent 102, extending laterally beyond the longitudinal side portions 107 and 107' to define longitudinal side edges 110 and 112. The longitudinal edges 110 and 112 can have any length ranging from a few millimeters to the entire length of the sanitary napkin 100. As used herein, the term "length" means the distance measured from one transverse end to the other transverse end and parallel to the longitudinal axis X—X of the sanitary napkin 100. The longitudinal side edges 110 and 112 can be asymmetrical about a transverse axis Y—Y but preferably they are symmetrical. The longitudinal side edges 110 and 112 can be linear, nonlinear or have some other geometric configurations such as triangular, semi-circular, etc.

Each longitudinal side edge 110 and 112 is gathered to form an integral longitudinal side barrier 114 and 116. Since the barriers 114 and 116 are similar in construction, only side barrier 114 will be discussed in detail, but it is to be understood as applying equally to side barrier 116. The side barrier 114 can be formed by folding the baffle 108 one or more times along a longitudinal line to form an accordion configuration barrier (not shown). Preferably, the side barrier 114 is formed by rolling the longitudinal side edge 110, and more preferably, spirally winding the longitudinal side edge 110 inward toward the longitudinal central axis X—X, and most preferably the longitudinal side edge 110 is spirally wound toward the body-facing surface 104. The length of the side barrier 114 is substantially determined by the length of the longitudinal side edge 110. The height of the integral side barrier 114 can be adapted for its intended use. The height of the barriers 114 is measured from a lowermost surface 118 to an uppermost surface 120. Since one intended function of the side barrier 114 is to improve side leakage protection, the side barrier 114 should have a height where the upper most surface 120 extends above the plane of the garment-facing surface 106 and preferably, it is substantially parallel to the plane of the bodyfacing surface 104, and more preferably, it is above the plane of the bodyfacing surface 104.

Referring to FIG. 6, the side barrier 114 has a vertical central axis Z—Z that substantially divides the side barrier 114 into an inside segment 122 and an outside segment 124. The inside segment 122 is positioned proximate the longitudinal side portion 107 while the outside segment 124 is positioned distally from the longitudinal side portion 107. The side barrier 114 can be hydrophilic, hydrophobic or a combination thereof. Preferably, the inside segment 122 is hydrophilic and the outside segment 124 is hydrophobic. This arrangement allows the side barrier 114 to enhance the absorbent capacity of the sanitary napkin 100 without adding substantial absorbent material to the absorbent 102. Another advantage to this arrangement is that placement of the sanitary napkin 100 in the crotch portion of the undergarment does not have to be as precise to maintain the efficacy of the sanitary napkin 100. The inside segment 122 can be positioned so that it resides adjacent to the longitudinal side portion 107 or spaced a distance therefrom up to about 25 millimeters, and preferably is spaced a distance of about 2 millimeters to about 15 millimeters from the longitudinal side portion 107.

Referring again to FIG. 4, one skilled in the absorbent art will recognize that by utilizing this invention one can construct an integral side barrier 114 having unique configurations. Depending upon the lateral extension of the longitudinal side edge 110, for example, by using an irregularly shaped longitudinal side edge 110, the side barrier 114 can have varied height dimensions. In this manner, one can customize the location of the barrier, improve side leakage protection in those areas where needed, and enhance the comfort of the sanitary napkin 100.

In the sanitary napkin 100, the absorbent 102 provides a means for absorbing the menstrual fluid. The total absorbent capacity of the absorbent 102 should be compatible with the predetermined exudate loading in the intended use of the sanitary napkin 100. Furthermore, the size and shape of the absorbent 102 can be varied. For example, the absorbent 102 can be rectangular, oval, racetrack or any other geometrical shape known in the absorbent art.

The absorbent 102 is generally made from one or more materials that, in combination, are substantially hydrophilic, compressible, conformable and non-irritating to the wearer's skin. Acceptable materials are well known in the art and include, for example, various natural or synthetic fibers, wood pulp fibers, regenerated cellulose or cotton fibers, or a blend of pulp and other fibers, meltblown polymer, such as polyester, and polypropylene. The absorbent layers may also be comprised of other well-known materials used in absorbent articles, including multiple layers of cellulose wadding, rayon fibers, cellulose sponge, hydrophilic synthetic sponge, such as polyurethane, and the like.

The absorbent 102 may contain superabsorbents which are effective in retaining body fluids. Superabsorbents have the ability to absorb a large amount of fluid in relation to their own weight. Typical superabsorbents used in absorbent articles, such as sanitary napkins, can absorb anywhere from about 5 to about 60 times their weight in body fluids.

Referring again to FIG. 6, the baffle 108 may be constructed from any desired material that is liquid-impermeable on the undergarment facing side and preferably will permit the passage of air and moisture vapor out of the sanitary napkin 100 while blocking the passage of body fluids. A good material is a micro-embossed, polymeric film, such as polyethylene or polypropylene having a thickness of about 0.001 to about 0.005 of an inch (0.025 to 0.13 millimeters). Bicomponent films can also be used as well as woven and nonwoven fabrics which have been treated to render them liquid-impermeable. Another suitable material is a closed cell polyolefin foam. For example, a closed cell polyethylene foam having a thickness ranging from about 0.5 millimeters to about 10 millimeters.

The sanitary napkin 100 may include other features such as cover 126. Generally, the cover 126 is provided for comfort and conformability and directs fluid to the underlying absorbent 102. The cover 126 can be constructed from a relatively non-absorbing fluid pervious material. The cover 126 can be constructed of any woven or nonwoven material which is easily penetrated by body fluid contacting its surface. Preferably, the cover 126 is made of a material which allows the passage of fluid without wicking it appreciably in a horizontal plane parallel to the cover 126. Furthermore, the cover 126 should retain little or no fluid in its structure so that it provides a relatively dry surface next to the skin. Generally, the cover 126 is a single sheet of material having a width sufficient to overlie the bodyfacing surface 104 of the absorbent 102. Preferably, the cover 126 extends to the longitudinal side edges 110 and 112 and is secured to the baffle 108. The cover 126 can be secured to the baffle 108 using any suitable method that does not leave a hard, uncomfortable residue that would be annoying to the wearer. Methods for joining the various materials are well known to those skilled in the art and include the use of pressure sensitive adhesives, hot melt adhesives, double-sided tape, ultra sonic bonding, and heat sealing to name a few. Adhesives, such as the hot melt adhesives can be applied in a uniform manner and as a continuous or non-continuous layer.

The cover 126 can be constructed of bonded carded webs of polyester, polypropylene, polyethylene, nylon, or other heat-bondable fibers. Other polyolefins, such as copolymers of polypropylene and polyethylene, liner low-density polyethylene, finely perforated film webs and net material also work well. Other suitable materials are composite materials of polymer and a nonwoven fabric material. The composite sheets are generally formed by extrusion of polymer onto a web of spunbond material to form an integral sheet. This material is preferred because the outer fabric surface is not irritating to the skin of the wearer and has a cushion feel.

Another preferred material for the cover 126 is a spunbond web of polypropylene. The web can contain about 1 to 6 percent titanium dioxide pigment to give it a clean white appearance. The most preferred polypropylene webs have a weight of between about 10 and 40 grams per square meter. Desirably, the weight is between about 20 and about 35 grams per square meter.

The liquid-permeable cover 126 can also contain a plurality of apertures (not shown) formed therein. Such apertures should be sized so fluid can pass through the cover 126 and into the absorbent 102. The apertures can be arranged longitudinally or can be zoned or localized to the area intended to be insulted with the body fluid, if desired. The apertures are intended to increase the rate at which body fluids can penetrate down into the absorbent 102. This helps maintain a perceivably drier surface for the cover 126 than when the apertures are not present. Therefore, while the apertures are not essential, a functional advantage is obtained by their use.

The liquid-permeable cover 126 can also be treated with a surfactant to make it more hydrophilic and, thereby, aid in the absorption of the liquid. The surfactant can include topical additions or internally applied materials like polysiloxanes.

Referring to FIGS. 7-10 a sanitary napkin 200 is depicted illustrating an alternative embodiment of this invention. The sanitary napkin 200 has a liquid-permeable cover 202 with a body-facing surface 204, a liquid-impermeable baffle 206 and an absorbent 208. The absorbent 208 has two longitudinal side portions 210 and 210'.

Figure 9:
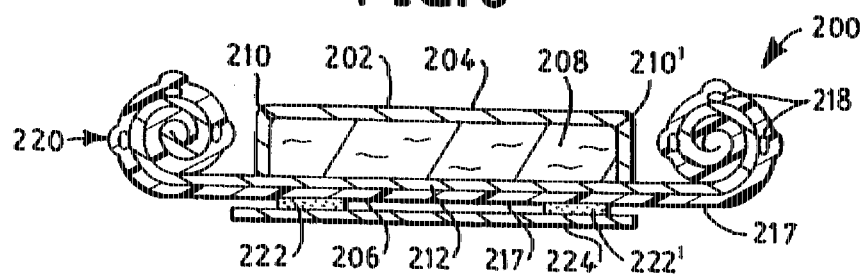
FIG. 9 is a cross-sectional view of the absorbent article taken along line 9—9 of FIG. 8.

Referring to FIG. 9, the sanitary napkin 200 further includes a resilient layer 212. The resilient layer is positioned between the cover 202 and baffle 206, preferably, it is the adjacent to the absorbent 208, and more preferably it is between the baffle 206 and the absorbent 208. As shown, the resilient layer 212 and baffle 206 extend laterally outward relative to longitudinal side portions 210 and 210' of the absorbent to be slightly more expansive than the absorbent 208. The baffle 206 and resilient layer 212 form longitudinal side edges 214 and 216. The resilient layer 212 can be hydrophilic or hydrophobic and can provide added absorbency and/or resiliency to the sanitary napkin 200.

Desirably, the resilient layer 212 can extend beyond the longitudinal side portions 210 and 210' of the absorbent to be coterminous with the cover 202 or the baffle 206. The resilient layer 212 may comprise a thin layer of absorbent material, such as, tissue, fabric or the like, made of cellulosic fibers. Because such material is provided as a safety measure and is only required to contain escaped fluid, it does not need to have a significant absorbent capacity relative to the absorbent 208. Another material is a meltblown polypropylene layer having a thickness of about 0.3 mm to about 1.0 mm, preferably about 0.4 to about 0.6 and having a weight of about 30 grams per square meter (gsm) to about 200 gsm, and preferably about 50 gsm to about 100 gsm. Such material is available from the Kimberly-Clark Corporation having offices at 401 North Lake Street, Neenah, Wis. and having a raw material specification number of 6103. A preferred material is a multicomponent, nonwoven polymer fabric as described in the patent application having U.S. Ser. No. 07/933,444 filed on Aug. 21, 1992 entitled "Nonwoven Multicomponent Polymer Fabric and Method of Making Same" and assigned to the present assignee, the entire disclosure of which is incorporated herein by reference.

A suitable hydrophobic material for use as a resilient layer 212 is any light weight polyolefin foam material. Such foams can be open or closed cell. Suitable foams include polyurethane and crosslinked or non-crosslinked polyolefin foams. Desirably, the foam is a polypropylene or a polyethylene foam, with polyethylene being preferred. Particularly preferred is a non-crosslinked polyethylene foam.

The foam can have a thickness ranging from about 0.381 millimeters to about 6.35 millimeters, preferably from about 0.51 millimeters to about 1.54 millimeters, and more preferably, from about 0.76 millimeters to about 1.27 millimeters, and most preferably, 0.76 millimeters to about 1.02 millimeters.

The foam can have a density ranging from about 0.0225 $gm/cm^3$ to about 0.0962 $gm/cm^3$, preferably ranging from about 0.0322 $gm/cm^3$ to about 0.0642 $gm/cm^3$, and most preferably from about 0.0354 $gm/cm^3$ to about 0.0482 $gm/cm^3$.

Figure 10:
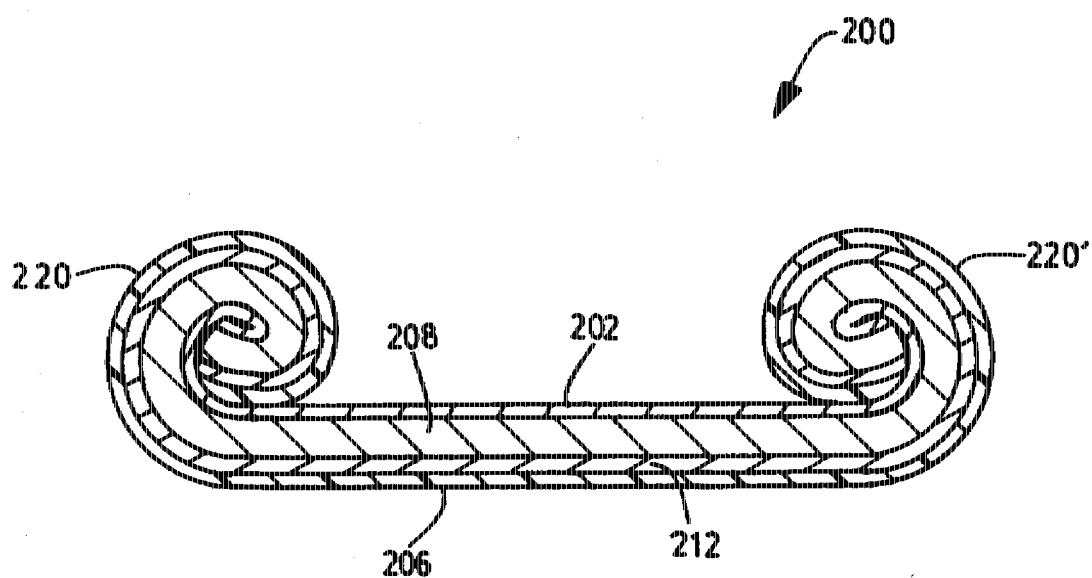
FIG. 10 is cross-sectional view of an alternative embodiment of the absorbent article.

Referring to FIG. 10, another embodiment of the absorbent article 200 is illustrated wherein the cover 202, baffle 206, the absorbent 208 and resilient layer 212 are laterally coextensive. The side edges are then rolled or spirally wound inward to form integral side barriers 220 and 220'.

Referring again to FIGS. 7-9, since the longitudinal side edge 214 and 216 are similar only side edge 214 will be described further. The longitudinal side edge 214 can have any length ranging from a few millimeters to extending the entire length of the sanitary napkin 200. The longitudinal side edge 214 can be linear, non-linear or have any other geometric configuration such as semi-circular, triangular and the like.

Disposed on the laterally-extending material between the longitudinal side portion 210 and the longitudinal side edge 214 is at least one longitudinal oriented tensioning member 218. Tensioning member 218 can be secured to either the body-facing surface 204 of the cover 202 or to a garment-facing surface 217 of the baffle 206. Alternatively, the tensioning member 218 can be secured between the cover 202 and baffle 206. The tensioning member 218 can be secured to the laterally-extending material by means well known in the art, such as, for example, using adhesives or a discontinuous ultrasonic bond.

The tension member 218 can be one or more elastic strips. If more than one elastic strip is utilized, it is preferred that the strips be spaced apart. The elastic strip is under tension prior to its securement to the laterally-extending material. Relative to its relaxed state, the elastic strip can be elongated up to 50% and preferably 100% prior to securing the elastic strip the to laterally-extending material. For the purposes of comfort, it is desired that the elastic strip have a width ranging from about 1 mm to about 7 mm in width, and preferably about 4 mm. Elastic having a width much greater than about 7 mm tends to chafe and become uncomfortable for the wearer.

Another method of introducing elastic is by utilizing an extrudable elastic which can be initially extruded as a liquid and upon cooling becomes both an adhesive and an elastic. This eliminates the separate step of adhesively bonding the strips of elastic to either side. An example of such a product is described in U.S. Pat. No. 4,259,220 assigned to H. B. Fuller Co. in St. Paul, Minn. the disclosure of which is incorporated herein by reference and made a part hereof.

The longitudinal side edge 214 is then gathered inward toward the absorbent 208 and more preferably, toward the bodyfacing surface 204 to form a liquid side barrier 220. Preferably, the side barrier 220 is formed by rolling and more preferably, spirally winding the longitudinal side edge 214. To assist in rolling the longitudinal side edge 214, a formed member can be used, (not shown). The formed member can have any geometrical configuration but preferably, is curved to facilitate rolling. The formed member can have a width dimension of from about 2 mm to about 12 mm. A preferred formed member is a rod shaped polyurethane foam having a diameter of about 3 mm to about 5 mm and a length substantially coinciding with the length of the longitudinal side edge 214.

The tensioning member 218 advantageously imparts to the sanitary napkin 200 a concave shape to the bodyfacing surface 204. This preferred configuration will provide a better fit to the body of the wearer. Preferably, the tension member 218 urges the side barrier 220 to rise forming an arcuate surface. As used herein the term "arcuate" means that when one transverse end of the sanitary napkin 200 is placed on a planar surface, the angle formed by the outer profile of other transverse end and the plane upon which the sanitary napkin 200 rests is between 10 degrees and 90 degrees.

The sanitary napkin 10 is about 150 millimeters (mm) to about 300 mm long and about 50 mm to about 175 mm wide at its widest point. The sanitary napkin 10 has an hourglass configuration but can include such shapes as rectangular, oval, racetrack, dogbone and the like.

Referring again to FIG. 9, the sanitary napkin 200 can be provided with attachment adhesive 222 and 222' applied to the garment-facing surface 217 of the baffle 206. The adhesive 222 and 222' can be made from any known pressure-sensitive material. As used herein the term "pressure sensitive" refers to any releasable adhesive or releasable tenacious means. Adhesive compositions suitable for sanitary napkins, includes, for example, the water-based pressure-sensitive adhesives such as acrylate adhesives. Alternatively, the adhesive may comprise rapid setting thermoplastic "hot melt", rubber adhesives or two-sided adhesive tape. As is customary in the art, the adhesive 222 and 222' can be covered by a protective release liner 224 such as a Kraft paper that is silicone coated.

In use, the wearer removes the release liner 224 and attaches the sanitary napkin 200 to the inside surface of her undergarment. The adhesive strips 222 and 222' allow the sanitary napkin 200 to remain in position to receive discharged liquids.

While the particular embodiments of the present invention have been illustrated and described, it would be obvious to those skilled in the art that various other changes and modifications can be made without departing from the spirit and scope of this invention. It is therefore intended to cover in the appended claims all such changes and modifications that are within the spirit and scope of this invention.

We claim:

1. An absorbent article comprising:
    a) an absorbent having a body-facing surface and a garment-facing surface; and
    b) a liquid-impermeable baffle secured to said garment-facing surface, said absorbent and said baffle having a coextensive width extending laterally outward relative to a longitudinal centerline to define longitudinal side edges, said longitudinal side edges being spirally wound to form integral longitudinal side barriers.

2. The absorbent article of claim 1 wherein said longitudinal side edges are spirally wound inward toward said absorbent to form said integral barriers.

3. The absorbent article of claim 1 further comprising a liquid-permeable cover secured to said body-facing surface of said absorbent.

4. The absorbent article of claim 1 wherein said integral barriers have an upper-most portion extending above a plane of said garment-facing surface.

5. The absorbent article of claim 1 further comprising tensioning means for imparting a concave curvature along a longitudinal axis toward said body-facing surface, said tensioning means being secured to at least one of said integral barriers.

6. The absorbent article of claim 1 further comprising a resilient member positioned between said body-facing surface and said baffle, said resilient member having a width that is coextensive with said absorbent and said baffle and extending laterally outwardly to define said longitudinal side edges, said edges being spirally wound inward to form said integral longitudinal side barriers.

7. The absorbent article of claim 6 wherein said resilient member is hydrophilic.

8. The absorbent article of claim 6 wherein said resilient member is hydrophobic.

9. An absorbent article comprising:
    a) a liquid-permeable cover having a body-facing surface;
    b) a liquid-impermeable baffle having a garment-facing surface; and
    c) an absorbent positioned between said cover and said baffle, said absorbent having longitudinal side portions wherein at least one of said cover or said baffle extend laterally beyond said longitudinal side portions to form longitudinal side edges, said longitudinal side edges being spirally wound inward to form integral longitudinal side barriers.

10. The absorbent article of claim 9 wherein said longitudinal side edges are spirally wound inward toward said garment-facing surface.

11. The absorbent article of claim 9 wherein said longitudinal side edges are spirally wound toward said body-facing surface.

12. The absorbent article of claim 9 wherein both said cover and said baffle extend laterally beyond said longitudinal side portions to form said longitudinal side edges.

13. The absorbent article of claim 9 wherein said integral barriers have an upper-most portion that extends above a plane of said body-facing surface of said cover.

14. The absorbent article of claim 9 further comprising a resilient layer positioned between said cover and said baffle and said resilient layer extends laterally outward beyond said longitudinal side portions of said absorbent.

15. The absorbent article of claim 14 wherein said resilient layer is hydrophilic.

16. The absorbent article of claim 14 wherein said resilient member is hydrophobic.

17. The absorbent article of claim 9 wherein each integral side barrier has a vertical center line dividing said integral side barrier into an inside segment and an outside segment, said inside segment is positioned proximate said longitudinal side portion of said absorbent and said outside segment is positioned distally from said longitudinal side portion, said inside segment being at least partially hydrophilic.

18. The absorbent article of claim 7 wherein said inside segment is spaced a predetermined distance from said longitudinal side portion.

19. The absorbent article of claim 9 further comprising tensioning means for imparting a concave curvature along a longitudinal axis toward said body-facing surface, said tensioning means being secured to at least one of said integral barriers.

* * * * *